United States Patent [19]

Freeman

[11] E Patent Number: Re. 31,640

[45] Reissued Date of Patent: Aug. 7, 1984

[54] [NEUTRAL] BUOYANCY INTRAOCULAR LENS DEVICE

[76] Inventor: Jerre M. Freeman, Ste. 501, Crew Wing, 176 S. Bellevue, Memphis, Tenn. 38104

[21] Appl. No.: 44,032

[22] Filed: May 31, 1979

Related U.S. Patent Documents

Reissue of:

[64] Patent No.: 4,077,071
Issued: Mar. 7, 1978
Appl. No.: 666,651
Filed: Mar. 15, 1976

[51] Int. Cl.[3] ..... A61F 1/16; A61F 1/24

[52] U.S. Cl. ..... 3/13

[58] Field of Search ..... 3/13, 1; 351/160

[56] References Cited

U.S. PATENT DOCUMENTS

| | | | |
|---|---|---|---|
| 2,834,023 | 5/1958 | Lieb | 3/13 |
| 3,711,870 | 1/1973 | Deitrick | 3/13 |
| 3,906,551 | 9/1975 | Otter | 3/13 |
| 3,925,825 | 12/1975 | Richards et al. | 3/13 |
| 3,979,780 | 9/1976 | Boniuk | 3/13 |
| 4,010,496 | 3/1977 | Neefe | 3/13 |

OTHER PUBLICATIONS

"Artiphakia and Aniseikonia" by R. C. Troutman, American Journal of Ophthalmology, vol. 56, No. 2, Oct. 1963, pp. 630–639.

"A Weightless Iseikonic Intraocular Lens" by Richard O. Binkhorst et al, American Journal of Ophthalmology, vol. 58, No. 1, Jul. 1964, pp. 73–78.

"The Weightless Intraocular Lens" by R. C. Troutman, Ophthalmic Surgery, vol. 8, No. 3, Jun. 1977, pp. 153–155, 3–13.

*Primary Examiner*—Ronald L. Frinks
*Attorney, Agent, or Firm*—Bradford E. Kile

[57] ABSTRACT

A neutral buoyancy intraocular lens device, adapted for implantation in a human eye and having an optical lens portion and support members attached thereto for holding the lens in place, is provided with a portion having a mean density lower than the density of the aqueous humor of the eye and a size large enough to decrease the mean density of the entire device to substantially the same as the aqueous humor of the eye to produce neutral buoyancy relative thereto, thereby increasing the compatibility of the device with the human user's eye and reducing trauma to the eye. The low-density portion may be an integral part of the lens and support structure, or may be a separate member attached thereto, and the lower mean density may be achieved by the use of a void or a relatively low density material.

22 Claims, 6 Drawing Figures

[NEUTRAL] BUOYANCY INTRAOCULAR LENS DEVICE

Matter enclosed in heavy brackets [ ] appears in the original patent but forms no part of this reissue specification; matter printed in italics indicates the additions made by reissue.

BACKGROUND OF THE INVENTION

The present invention relates generally to intraocular lens devices adapted for implantation in a human eye.

Intraoccular lens devices (hereinafter also referred to as IOLs) are well known and in many forms have been successfully implanted in human eyes following cataract surgery after the natural crystalline lens of the eye has been removed, as has been described for example in J. Jaffe, "Current Status of Intraocular Lenses," 51 Eye, Ear, Nose and Throat Monthly 290–96 (1972). However, excess weight and size of the IOLs caused failure of some of the early implants, and the ultimate success of this technique was due in part to the reduction in weight of the lens device.

Even though the weight of IOLs has been reduced in more recent devices developed in the art, the applicant is of the belief that a significant added advantage could be gained if their weight relative to the fluid inside the eye could be reduced to zero, that is, if the lens could be provided with neutral buoyancy with respect to the aqueous humor of the eye. Such a neutral buoyancy condition of the intraocular lens (that is, a condition in which the mean density of the IOL is equal to the density of the aqueous humor) would, it is felt, reduce the tremor, or shake, due to the fast saccadic movement of the eye, which in turn would likely reduce iris irritation and hence, possibly, a type of recurrent traumatic iritis. Neutral buoyancy also would tend to reduce the likelihood of the lens becoming a semi-missile inside the eye in the event of severe ocular trauma such as occurs in a car accident or other unexpected event causing a sudden impact to the head.

The natural crystalline lens itself has weight within the eye, that is, it does not achieve neutral buoyancy, but due to the hundreds of zonule fibrils coming from the ciliary body that support its entire periphery, the natural crystalline lens moves very little with large or sudden movements of the eye. However, some IOLs do not share this broad support, but instead are supported only by a few points of contact with the iris which carry the entire weight of the IOL. For example, the IOL may be supported by the pupilary sphincter, or by a suture, arm or loop attaching the IOL to the iris. Although the weight of the IOL may be very small, the few support points of iris contact experience high-pressure loading which can contribute to pressure necrosis and atrophy of the fragile iris.

Although some IOLs are supported entirely by the lens capsule zonular fibrils and therefore do not produce the aforementioned problems associated with the iris, this fixation technique is uncommonly used since the danger of dislocation of an implant supported solely by the lens capsule is high. Therefore irido-capsular fixation is more commonly utilized, whereby the lens is partially supported by the iris as well as the posterior capsular of a natural lens. In the latter case it would be desirable to utilize a lens of neutral buoyancy to lower the pressure imposed on the fragile iris.

SUMMARY OF THE INVENTION

The present invention eliminates the aforementioned problems associated with implanting an IOL resulting from the weight of the implanted device by the technique, applicable to an IOL of virtually any design, of providing the device with a neutral buoyancy relative to the aqueous humor of the eye. By way of example the neutral buoyancy of the IOL may be achieved by providing its structure with portions having a mean density less than the density of the aqueous humor of the eye, through the medium of employing lens elements made of low-density material or having hollow portions which are evacuated or filled with an inert gas, in a sufficient amount that the mean density of the entire IOL structure is substantially equal to the density of the aqueous humor.

In one exemplary embodiment the IOL includes anterior or posterior laterally-protruding loops attached to an optical lens which are used for supporting the lens, and the neutral buoyancy is achieved by utilizing hollow loops made from nonexpandable, noncollapsible metal. The loops are made of hollow tubes each having a length sufficient to provide the necessary support of the lens in the eye and having an inside diameter calculated to provide enough volume within the loops that the combined lens and loops will displace an amount of fluid within the eye which is as heavy or heavier than the IOL. The two ends of each loop are sealed and attached to the lens, which typically is made of a highly-refined pure polymer of plastic such as polymethyl methacrylate. The mean density of the sealed tubes should be less than the density of the aqueous humor in order to achieve the objectives of this invention.

An alternative embodiment utilizes, in addition to support members, a small hermetically sealed chamber attached to the IOL to serve as a float. The mean density of the sealed chamber should be less than that of the aqueous humor, and preferably the chamber should be large enough that the volume of fluid displaced by the IOL is equal or greater in weight than the IOL.

Another alternative embodiment utilizes peripheral arms attached to an optical lens, the arms being made of an inert material having less density than the aqueous humor of the eye, or of an inert material having bubbles of an inert gas contained in a matrix of chambers formed therein to provide a low density material in sufficient quantity for neutral buoyancy of the IOL.

While materials for producing the optical lens portion of an IOL have heretofore been chosen for their relatively light weight, as well as their optical properties and tissue inertness, for example polymethyl methacrylate has been found to be particularly suitable for use in IOLs, there are other inert optical materials, such as crown glass, that have superior optical qualities but due to their heavier weight, have not previously been used. The adoption of the principles of the present invention may render more feasible the application of these heavier, optically superior materials to IOL devices by effectively reducing the overall buoyancy weight of the device to near zero when suspended in the eye fluid.

Therefore, it is a principal objective of the present invention to provide an intraocular lens device having a lower mean density than heretofore achieved in order to increase its compatibility with a human user's eye and reduce trauma to the user's eye.

It is a particular objective of the present invention to provide an improved intraocular lens device which incorporates portions having less mean density than the aqueous humor of a human eye to balance other portions having higher mean density than the aqueous humor, thereby resulting in neutral, or near neutral buoyancy of the lens device.

The foregoing objectives, features and advantages of the present invention will be more readily understood upon consideration of the following detailed description of the invention taken in conjunction with the accompanying drawings.

DETAILED DESCRIPTION OF THE INVENTION

Figure 1:
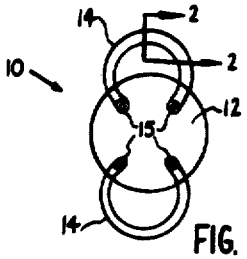
FIG. 1 is a front view of an embodiment of the intraocular lens device (IOL) according to the present invention utilizing hollow support loops for achieving neutral buoyancy.
Figure 2:
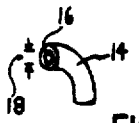
FIG. 2 is a perspective view of a portion of a support loop of the embodiment taken along the line 2—2 of FIG. 1.

Referring to FIGS. 1 and 2, a first embodiment 10 of the intraocular lens device incorporating the teachings of the present invention comprises an optical lens portion 12 made of a highly-refined pure polymer of plastic (for example, polymethyl methacrylate), crown glass or some other relatively inert transparent material having desirable optical qualities, which is shaped with one or more curved surfaces to produce the optical effect necessary for replacement of a natural human crystalline lens, and one or more support loops 14 attached to the optical lens 12 for holding the lens in place inside a human eye. The support loops are made of nonexpandable, noncollapsible metal tubing which may be produced by extrusion, as is commonly known to the art. The loops 14 are made in lengths appropriate for holding the lens in the eye and with their ends 15 sealed, leaving the interior of the loops evacuated or filled with a [gass] *gas*.

The amount of buoyancy provided by the loops 14 will depend upon the number of loops attached to the apparatus 10, the density of the material used to manufacture the loops, and the volume of the hollow space 16 within the loops, which in turn is a function of the length of the loops and their inside diameter 18. Therefore, given the number of loops and their lengths required adequately to hold the lens in the eye, and the density characteristic of the material with which the loops are to be manufactured, the inside diameter 18 should preferably be calculated to provide sufficient volume to produce neutral buoyancy for the entire IOL. To achieve neutral buoyancy the inside volume of the loops should be made such that the mean density of the loops is less than the density of the aqueous humor of the eye, thereby reducing the overall mean density of the IOL to approximately the density of the aqueous humor. It will be recognized by those skilled in the art that many different combinations and orientations of loops might be utilized, that a gas may be contained inside the loops, and that the calculation of the desired mean density for the resultant IOL device must take these factors into account. It will also be recognized that there is a possibility that different individuals may have aqueous humor of different respective densities, in which case an IOL may be fabricated with a mean density suitable for a specific individual, or selected for a specific individual from among several IOLs having different mean densities.

Figure 3:
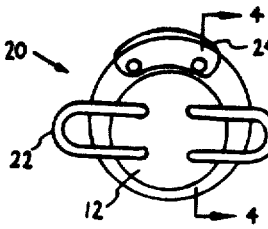
FIG. 3 is a second embodiment of an IOL according to the present invention utilizing a float chamber for achieving neutral buoyancy.
Figure 4:
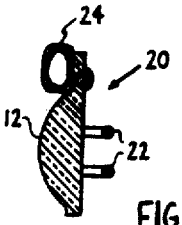
FIG. 4 is a sectional view of the second embodiment taken along the line 4—4 of FIG. 3.

Turning now to FIGS. 3 and 4, a second embodiment 20 of the present invention is shown, having an optical lens portion 12 similar to the corresponding portion of the first embodiment 10 and support members 22 attached to the optical lens for holding it in place in the eye. In addition, the second embodiment 20 of the IOL apparatus includes a low mean density member comprising a hollow hermetically-sealed chamber 24 manufactured of metal or some appropriate inert substance, and having an inside volume sufficient to provide the IOL apparatus with neutral, or near neutral, buoyancy relative to the aqueous humor.

Figure 5:
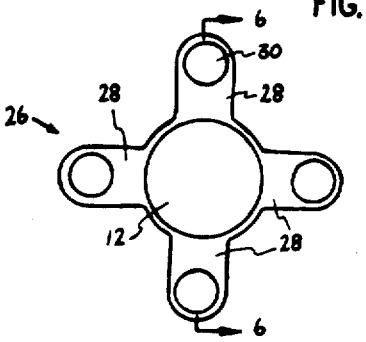
FIG. 5 is a front view of a third embodiment of an IOL according to the present invention utilizing low-density lateral arms for achieving neutral buoyancy.
Figure 6:
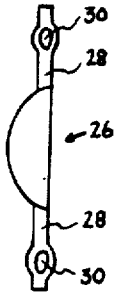
FIG. 6 is a sectional view of the third embodiment taken along line 6—6 of FIG. 5.

A third embodiment 26, shown in FIGS. 5 and 6, utilizes a similar optical lens 12, having attached thereto one or more laterally protruding support arms 28 made of a material, or containing pockets 30 of inert gas, having less mean density than the aqueous humor of a human eye. Similarly to the aforementioned embodiments, the arm material, or the gas in the arms, should be provided in a quantity sufficient to give the entire IOL a mean density less than or equal to the density of the aqueous humor in order to produce the desired condition of neutral buoyancy.

In addition to the afore-described specific exemplary embodiments incorporating the present invention, other arrangements for coupling a low mean density member to an optical lens to produce an IOL having an overall mean density equal to or less than the density of the aqueous humor of a particular individual's eye might also be utilized without departing from the principles of this invention. Moreover, other methods of increasing the comfort of an IOL to its human user and reducing trauma to the user's eye resulting from an implanted IOL by providing an IOL with substantially neutral buoyancy within the eye might fall within the scope of this invention as well.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An intraocular lens device for implantation into a human eye, said lens device comprising:

(a) an optical lens suitable for replacing a human crystalline lens having a mean density greater than that of the aqueous humor of said human eye; and (b) buoyancy means external of and attached to said optical lens having a mean density less than the density of said aqueous humor for providing a plurality of irido-capsular support points on the posterior surface of the iris of said human eye to hold said optical lens in place when implanted into said human eye and for reducing the overall mean density of said lens device to substantially that of said aqueous humor.

2. The lens device of claim 1 wherein said buoyancy means includes an evacuated sealed chamber formed therein, said chamber having a volume sufficient to provide said buoyancy means with a mean density less than that of said aqueous humor.

3. The lens device of claim 1 wherein said buoyancy means includes a sealed chamber formed therein containing an inert substance having a density less than the mean density of said aqueous humor, said chamber containing a sufficient quantity of said inert substance to provide said buoyancy means with a mean density less than that of said aqueous humor.

4. The lens device of claim 1 wherein said buoyancy means comprises a plurality of projecting members external of and attached to said optical lens.

5. The lens device of claim 4 wherein said optical lens is of glass material.

6. The lens device of claim 5 wherein said optical lens includes a supportive surface for engaging the posterior capsular of said replaced human lens when implanted in said human eye.

7. An intraocular lens device for implantation into a human eye, said lens device comprising:

(a) an optical lens suitable for replacing a human crystalline lens having a mean density greater than that of the aqueous humor of said human eye;

(b) support means attached to said lens for providing a plurality of irido-capsular support points on the posterior surface of the iris of said human eye to hold said optical lens in place when implanted into said human eye; and (c) buoyancy means separated and apart from said support means, said buoyancy means being external of and attached to said optical lens having a mean density less than that of said aqueous humor for reducing the overall means density of said lens device to approximately that of said aqueous humor.

8. The lens device of claim 7 wherein said buoyancy means includes an evacuated sealed chamber formed therein, said chamber having a volume sufficient to reduce the overall mean density of said device to substantially that of said aqueous humor.

9. The lens device of claim 7 wherein said buoyancy means includes a sealed chamber formed therein containing an inert substance having a mean density less than that of said aqueous humor, said chamber containing a sufficient quantity of said inert substance to reduce the overall mean density of said device to substantially that of said aqueous humor.

*10. An intraocular lens device for implantation into a human eye, said lens device comprising:*

*an optical lens suitable for replacing a human crystalline lens, said optical lens having a mean density greater than the density of the aqueous humor of the human eye; and*

*support means attached to said lens for providing a plurality of support points at least within the posterior chamber of the human eye to hold said optical lens in place when implanted into the human eye, said support means having a density less than the density of the aqueous humor of the eye for providing at least a degree of buoyant uplift to said optical lens when said intraocular lens device is implanted into the human eye.*

*11. The lens device of claim 10 wherein said support means comprises:*

*a plurality of loop members formed from a material having a density less than the density of the aqueous humor of the human eye.*

*12. The lens device of claim 10 wherein said support means comprises:*

*a plurality of closed tubular loop members wherein the overall density of said closed tubular members has a density less than the density of the aqueous humor of the human eye.*

*13. The lens device of claim 10 wherein said support means comprises:*

*a plurality of members having at least one sealed chamber therein wherein the overall density of said support means has a density less than the density of the aqueous humor of the human eye.*

*14. An intraocular lens device for implantation into a human eye, said lens device comprising:*

*an optical lens suitable for replacing a human crystalline lens, said optical lens having a mean density greater than the density of the aqueous humor of the human eye; and*

*support means attached to said lens for providing a plurality of support points at least within the posterior chamber of the human eye to hold said optical lens in place when implanted into the human eye, said support means having a density less than the density of the aqueous humor of the eye for providing a buoyant uplift to said optical lens when said intraocular lens device is implanted into the human eye, said support means has a density relative to the density of the aqueous humor of the human eye to reduce the overall mean density of the intraocular lens device to near neutral buoyancy relative to the aqueous humor of the human eye.*

*15. An intraocular lens device for implantation into a human eye, said lens device comprising:*

*an optical lens suitable for replacing a human crystalline lens, said optical lens having a mean density greater than the density of the aqueous humor of the human eye; and*

*buoyancy means external of and attached to said optical lens, said buoyancy means having a density less than the density of the aqueous humor of the human eye and said buoyancy means adapted to extend at least in part into the posterior chamber of the human eye for providing at least a degree of buoyant uplift for the optical lens when the intraocular lens device is implanted into the human eye.*

*16. The lens device of claim 15 wherein said buoyancy means comprises:*

*a plurality of members formed from a material having a density less than the density of the aqueous humor of the human eye.*

*17. The lens device of claim 15 wherein said support means comprises:*

*a plurality of closed tubular loop members wherein the overall density of said closed tubular members has a density less than the density of the aqueous humor of the human eye.*

*18. The lens device of claim 15 wherein said support means comprises:*

*a plurality of members having at least one sealed chamber therein wherein the overall density of said support means has a density less than the density of the aqueous humor of the human eye.*

*19. An intraocular lens device for implantation into a human eye, said lens device comprising:*

*an optical lens suitable for replacing a human crystalline lens, said optical lens having a mean density greater than the density of the aqueous humor of the human eye; and*

*buoyancy means external of and attached to said optical lens, said buoyancy means having a density less than the density of the aqueous humor of the human eye and said buoyancy means adapted to extend at least in part into the posterior chamber of the human eye for providing a buoyant uplift for the optical lens when the intraocular lens device is implanted into the human eye, said support means having a density relative to the density of the aqueous humor of the human eye sufficient to reduce the overall mean density of the intraocular lens device to near neutral buoyancy relative to the aqueous humor of the human eye.*

*20. An intraocular lens device for implantation into a human eye, said lens device comprising:*

*an optical lens suitable for replacing a human crystalline lens, said optical lens having a mean density greater than the density of the aqueous humor of the human eye; and*

*buoyancy means external of and attached to said optical lens, said buoyancy means having a density less than the density of the aqueous humor of the human eye and said buoyancy means adapted to extend within at least one of the anterior and posterior chambers of the human eye for providing a buoyant uplift for the optical lens when the intraocular lens device is implanted into the human eye, said support means has a density relative to the density of the aqueous humor of the human eye to reduce the overall mean density of the intraocular lens device to near neutral buoyancy relative to the aqueous humor of the human eye.*

*21. An intraocular lens device for implantation into a human eye, said lens device comprising:*

*an optical lens suitable for replacing a human crystalline lens, said optical lens having a mean density greater than the density of the aqueous humor of the human eye; and*

*buoyancy means external of and attached to said optical lens, said buoyancy means comprising a plurality of members having a density less than the density of the aqueous humor of the human eye and said buoyancy means adapted to extend within at least one of the anterior and posterior chambers of the human eye for providing at least a degree of buoyant uplift for the optical lens when the intraocular lens device is implanted into the human eye.*

*22. The lens device of claim 21 wherein said buoyancy means comprises:*

*a plurality of members formed from a material having a density less than the density of the aqueous humor of the human eye.*

* * * * *